United States Patent [19]
Agee et al.

[11] Patent Number: 5,613,976
[45] Date of Patent: Mar. 25, 1997

[54] INSTRUMENT FOR MESH CUTTING OF THE FLEXOR RETINACULUM

[75] Inventors: John M. Agee, 77 Scripps Dr., Sacramento, Calif. 95825; Francis King, Sacramento, Calif.

[73] Assignee: John M. Agee, Sacramento, Calif.

[21] Appl. No.: 366,038

[22] Filed: Dec. 29, 1994

Related U.S. Application Data

[62] Division of Ser. No. 126,257, Sep. 24, 1993, Pat. No. 5,387,223.

[51] Int. Cl.⁶ .......................... A61B 17/04; A61B 17/32
[52] U.S. Cl. .......................... 606/150; 606/148; 606/170
[58] Field of Search ................... 606/167, 170, 606/172, 174, 184–186, 144, 148, 150; 128/898

[56] References Cited

U.S. PATENT DOCUMENTS

| | | | |
|---|---|---|---|
| 1,515,050 | 11/1924 | Jensen. | |
| 2,631,585 | 3/1953 | Siebrandt. | |
| 4,499,899 | 2/1985 | Lyons, III. | |
| 4,644,953 | 2/1987 | Lahodny et al. | 606/174 |
| 4,711,240 | 12/1987 | Goldwasser et al. | 606/174 |
| 4,819,620 | 4/1989 | Okutsu. | |
| 4,836,205 | 6/1989 | Barrett | 606/185 |
| 4,962,770 | 10/1990 | Agee et al. | 606/170 X |
| 4,963,147 | 10/1990 | Agee et al. | 606/170 |
| 4,971,067 | 11/1990 | Bolduc et al. | 606/170 X |
| 5,133,727 | 7/1992 | Bales et al. | 606/205 X |
| 5,179,963 | 1/1993 | Berger | 128/898 |
| 5,188,636 | 2/1993 | Fedotov | 606/144 |
| 5,197,971 | 3/1993 | Bonutti | 606/192 |
| 5,256,136 | 10/1993 | Suchlr | 606/21 |
| 5,269,796 | 12/1993 | Miller et al. | 606/167 |

FOREIGN PATENT DOCUMENTS

0209631  1/1968  U.S.S.R. .................. 606/186

*Primary Examiner*—Michael Powell Buiz
*Assistant Examiner*—Nancy Mulcare
*Attorney, Agent, or Firm*—Dean P. Edmundson

[57] ABSTRACT

Apparatus and method are described for selective cutting of the transverse carpal ligament of a patient. The instrument includes spaced-apart teeth which are supported on a first arm and a press member which is carried by a second arm. The teeth are prevented from contacting tissue when the first arm is inserted into, or retracted from, the carpal tunnel. After insertion of the first arm into the carpal tunnel, the teeth are exposed to the transverse carpal ligament and the first and second arms are moved towards each other to force the teeth into the transverse carpal ligament to perforate the ligament and enable it to elongate.

5 Claims, 9 Drawing Sheets

HOOK OF HAMATE

INSTRUMENT FOR MESH CUTTING OF THE FLEXOR RETINACULUM

This is a divisional of application Ser. No. 08/126,257 filed on Sep. 24, 1993, now U.S. Pat. No. 5,387,223.

FIELD OF THE INVENTION

This invention relates to surgical instruments. More particularly, this invention relates to surgical instruments for treatment of carpal tunnel syndrome.

BACKGROUND OF THE INVENTION

The carpal tunnel is formed by an arch of the eight wrist bones, spanned on its palmar surface by the transverse carpal ligament, known as the flexor retinaculum. The carpal tunnel functions as a mechanical pulley to provide the appropriate moment arms for the digital flexor tendons as they pass through the tunnel. The tendons can then transmit force out into the fingers and impart only an appropriate amount of tension to develop torque at the level of the wrist.

Within the carpal tunnel, these tendons are lubricated and nourished by two synovial membranes—the radial and the ulnar bursa. The median nerve also shares the carpal tunnel, and then it branches out to provide sensory innervation to the palmar surface of the thumb, index, long and a portion of the ring finger. In addition, a small motor branch of the median nerve supplies the thenar muscles, which are responsible for lifting the thumb into opposition with the fingers.

Carpal tunnel syndrome refers to numerous clinical signs and symptoms resulting from pressure on the median nerve inside the carpal tunnel. The typical etiology is increased pressure within the carpal tunnel, which interferes with the function of the median nerve. The patient experiences numbness and tingling in the fingers, together with pain that may radiate as far as the shoulder or base of the neck. Other symptoms include impaired grasping ability (due to sensory deprivation from the digits), loss of sleep from pain and numbness in the hand, and weakness or atrophy of the thenar muscles.

The pathology generally results from a swelling of the synovial membranes, which is typically idiopathic. Carpal tunnel syndrome can also be caused by pressure on the median nerve from rheumatoid arthritis or edema in the final trimester of pregnancy, or other diseases.

Many instances of carpal tunnel syndrome can be treated conservatively, typically with a resting splint and cortisone injection into the carpal tunnel. However, if symptoms persist and/or reoccur, or if the patient has severe sensory deficit or loss of functions in the thenar muscles, then surgical decompression of the nerve by release of the transverse carpal ligament is often indicated.

Surgical decompression has been accomplished, in early techniques, by a longitudinal incision paralleling the thenar crease. The incision was carried down through the skin, subcutaneous fat, and palmar fascia to divide the palmaris brevis muscle and then the transverse carpal ligament. Most cases do not require any surgical treatment within the carpal tunnel, other than the division of the ligament. Thereafter, the skin is sutured and the patient was frequently splinted for about three weeks.

In the frequent cases where the syndrome is occupationally related, i.e., where workmen's compensation is involved, the patient was usually disabled for six to eight weeks. If the patient was a manual laborer, two or three months may pass before the return to gainful employment. This post-operative morbidity is primarily due to persistent tenderness in the palm as the scar tissue matures. Most patients experience tenderness in the heel of their hand for four to six months following the surgery.

Previously, a few surgeons would release the carpal tunnel by inserting scissors through a transverse incision proximal to the carpal tunnel. The blind release by division of the ligament would then proceed from the proximal to the distal end. When successful, this technique would decompress the median nerve (without scarring the heel of the patient's hand) and would significantly decrease postoperative pain and morbidity.

However, transverse incision and blind release is not advisable, due to the risk of incomplete release of the carpal tunnel, or injury to the superficial arterial arch and/or the median nerve. The superficial palmar arterial arch lies just distal to the distal portion of the transverse carpal ligament. The motor branch of the median nerve, which controls thumb opposition, is typically on the distal radial extent of the carpal tunnel, although anomalies can allow it to penetrate the transverse carpal ligament in any of a number of positions and be subject to injury during blind release procedures or surgical release by any method.

More recently, an improved surgical instrument and technique for effecting carpal tunnel release has been described in U.S. Pat. Nos. 4,963,147; 4,962,770; and 5,089,000. The instrument is also useful in other surgical techniques. The instrument includes a probe in which a cutting blade and an optical system are disposed. After the probe has been inserted into a body cavity, the cutting blade is extended through a lateral aperture in the probe to a position adjacent the selected tissue, while allowing the tissue manipulation to be observed.

The surgical instrument and technique described in the foregoing patents is useful in effecting complete division of the flexor retinaculum under visual inspection, while minimizing the risk of injury to surrounding tissue. In using the instrument, an incision is made at one end of the carpal tunnel, and then the probe is inserted through the incision and positioned adjacent to the flexor retinaculum. The cutting blade is then elevated and the probe is withdrawn so that the flexor retinaculum is divided, thereby releasing the carpal tunnel. The optical system enables continuous observation of the portion of the cutting blade within its field of view.

There are a number of potential disadvantages associated with complete division of the transverse carpal ligament, including alteration of the arch formed by the carpal bones, complete interruption of the pulley effect created by the transverse carpal ligament (allowing the digital flexor tendons and/or median nerve to sublux palmarwardly between the cut edges of the transverse ligament), and exposure of the cut edges of the transverse carpal ligament such that scar tissue necessary for its healing in the lengthened position is more abundant and therefore potentially creating greater post-operative morbidity, pain and weakness.

Furthermore, there is no objective data establishing that maximum lengthening of the transverse carpal ligament through its complete surgical division and subsequent reconstitution by scar tissue is necessary. For example, mechanical structures such as the Achilles' tendon were historically released by complete division only to discover by further study that optimal function could be obtained by selective lengthening of the contracted muscle tendon unit (the so-called Z-plasty lengthening).

There has not heretofore been provided an effective technique or surgical instrumentation to facilitate releasing the carpal tunnel without complete division of the flexor retinaculum (i.e., transverse carpal ligament).

SUMMARY OF THE INVENTION

In accordance with the present invention there is provided an instrument and technique for selective cutting of the flexor retinaculum resulting in its relative lengthening so that the size of the carpal tunnel is increased, thereby decreasing the pressure within the carpal tunnel that impairs median nerve function. In one embodiment, the instrument comprises:

(a) a plurality of spaced-apart teeth members supported on a first arm member;

(b) protector means for selectively preventing the teeth members from being exposed such that the device can be inserted into and removed from the carpal tunnel without the teeth members injuring the tissues of the carpal tunnel;

(c) a press member carried by a second arm member in opposing relation to the teeth members; and (d) means for selectively moving the teeth members and the press member towards each other.

The teeth members on the first arm can be inserted into the carpal tunnel through a small incision at one end of the carpal tunnel (i.e., similar to the incision made for insertion of the surgical instrument described in the above-mentioned patents). When the teeth member are positioned beneath the transverse carpal ligament, the protector means is removed from the teeth, after which the teeth members are forced directly into the carpal ligament to selectively cut the ligament to enable it to stretch or lengthen.

The method and instrument of this invention provide for selective cutting of only limited portions of the transverse carpal ligament. This provides several advantages over prior techniques, including (a) prevention of excessive palmar displacement of the digital flexor tendons and/or median nerve created by the traditional complete release of the transverse carpal ligament; (b) avoiding entrapment of the median nerve and/or flexor tendons in a subcutaneous palmar position in which these structures are relatively or absolutely entrapped in scar tissue that occurs as a result of the healing process for the surgically divided transverse carpal ligament; (c) maintenance of relative stability of the entire transverse carpal ligament as a unit, i.e., the cut edges of the completely divided ligament can evert (turn outward or subcutaneously) as a result of the spread of the carpal tunnel, as well as the pull of the thenar and hypothenar muscle groups, particularly the thenar muscles on the radial side of the divided transverse carpal ligament; (d) preservation of a gliding surface on the deep side of the transverse carpal ligament for the digital flexor tendons and median nerve; and (e) potential decreased morbidity from greater stability of the origin of the muscles that arise from the transverse carpal ligament, particularly the thenar muscles responsible for thumb opposition, pinch and grasp.

Another advantage of the present invention is that the multiple cutting teeth of the device directly incise the transverse carpal ligament from dorsal to palmar through the substance of the ligament, thereby creating the least opportunity for injury to precious structures such as the median nerve. As contrasted with previously known devices, the device of this invention positions the cutting blades or teeth in a manner such that the blades cut only selected portions of the transverse carpal ligament. The blades are not exposed during insertion into, or withdrawal of the device from, the carpal tunnel. This eliminates or minimizes the opportunity for grabbing or cutting branches of the median nerve and flexor tendons.

Yet another advantage is that the height and disposition of the various teeth of the device can be selected to penetrate the varying depth of the transverse carpal ligament (which is thickest in the center and becomes thinner both proximally and distally). The optimally configured teeth of the device therefore penetrate through the depth of the ligament which is variable along its length from proximal to distal. This device is in sharp contrast to other currently available endoscopic devices which typically have their cutting mechanisms extend through the ligament to an extent which is adequate to incise the thicker mid-portion of the ligament while they simultaneously cut into and violate the palmar fascia and subcutaneous tissues from the distal and proximal ends of the carpal tunnel where the ligament is thinner.

Preferably the teeth members are present in spaced-apart rows, and preferably the teeth in one row are staggered or offset from the teeth in the adjacent row. In this manner, the perforations or incisions resulting in the carpal ligament in one row are offset from the perforations in an adjacent row. This is very desirable because it enables the transverse carpal ligament to easily stretch or lengthen without losing all of its pulley function.

Other advantages of the instrument and technique of the invention will be apparent from the following detailed description and the accompanying drawings.

BRIEF DESCRIPTION OF THE DRAWINGS

The invention is described in more detail hereinafter with references to the accompanying drawings, wherein like reference characters refer to the same parts throughout the several views and in which.

DETAILED DESCRIPTION OF THE INVENTION

In the drawings there is shown a surgical instrument 10 of the invention for selective cutting or perforating of the flexor retinaculum (i.e, the transverse carpal ligament). The instrument includes a lower arm 12 and an opposing upper arm 14. Two or more rows of spaced-apart teeth members 16 are carried on the lower arm. A press member 18 is carried on the upper arm in opposing relation to the teeth members, as illustrated.

Figure 10:
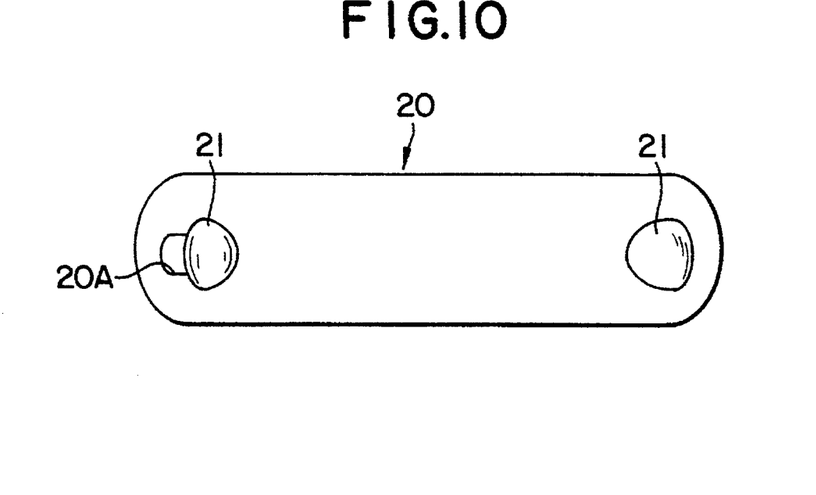
FIG. 10 is a bottom view of the press member of the instrument of FIG. 1.

Preferably the press member 18 comprises an elongated strip 20 which is fastened at its opposite ends to legs 18A and 18B. As shown in FIG. 10, the strip 20 includes an elongated aperture 20A at one end. Screws or posts 21 secure the strip 20 to legs 18A and 18B. See FIG. 10. Due to the elongated aperture 20A, the strip 20 can deflect and conform to the palm and heel of the hand when the press member is forced toward the teeth members during use of the instrument, as hereafter described. The height of member 20 relative to arm 12 may be adjusted by means of clamp 22 which releasably secures shank 19.

The upper and lower arms are preferably pivotably connected to each other. By moving arms 12A and 14A towards each other, the arms 12 and 14 are also caused to move towards each other, preferably in parallel planes.

Figure 1:
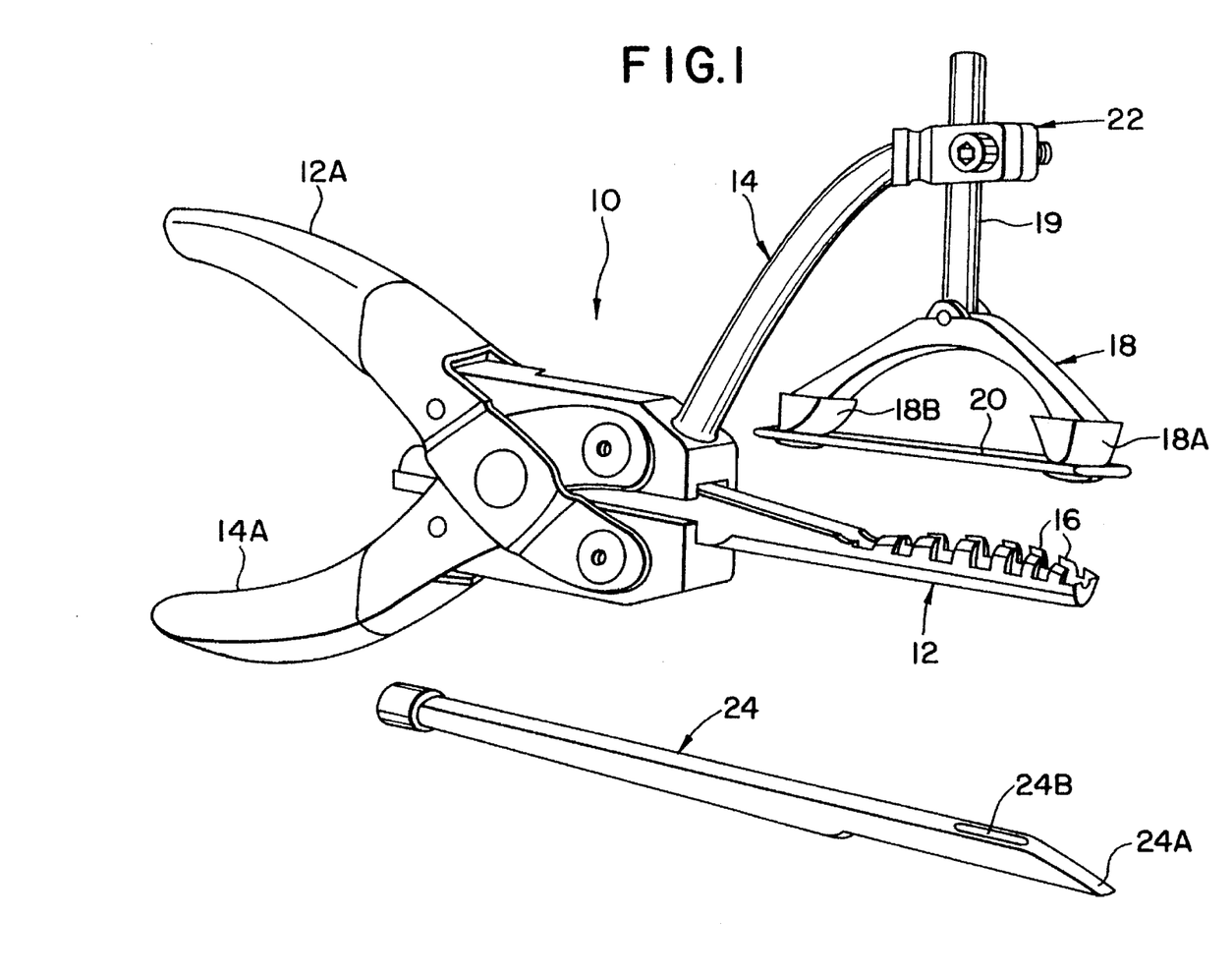
FIG. 1 is a perspective view of one embodiment of surgical instrument of this invention.
Figure 2:
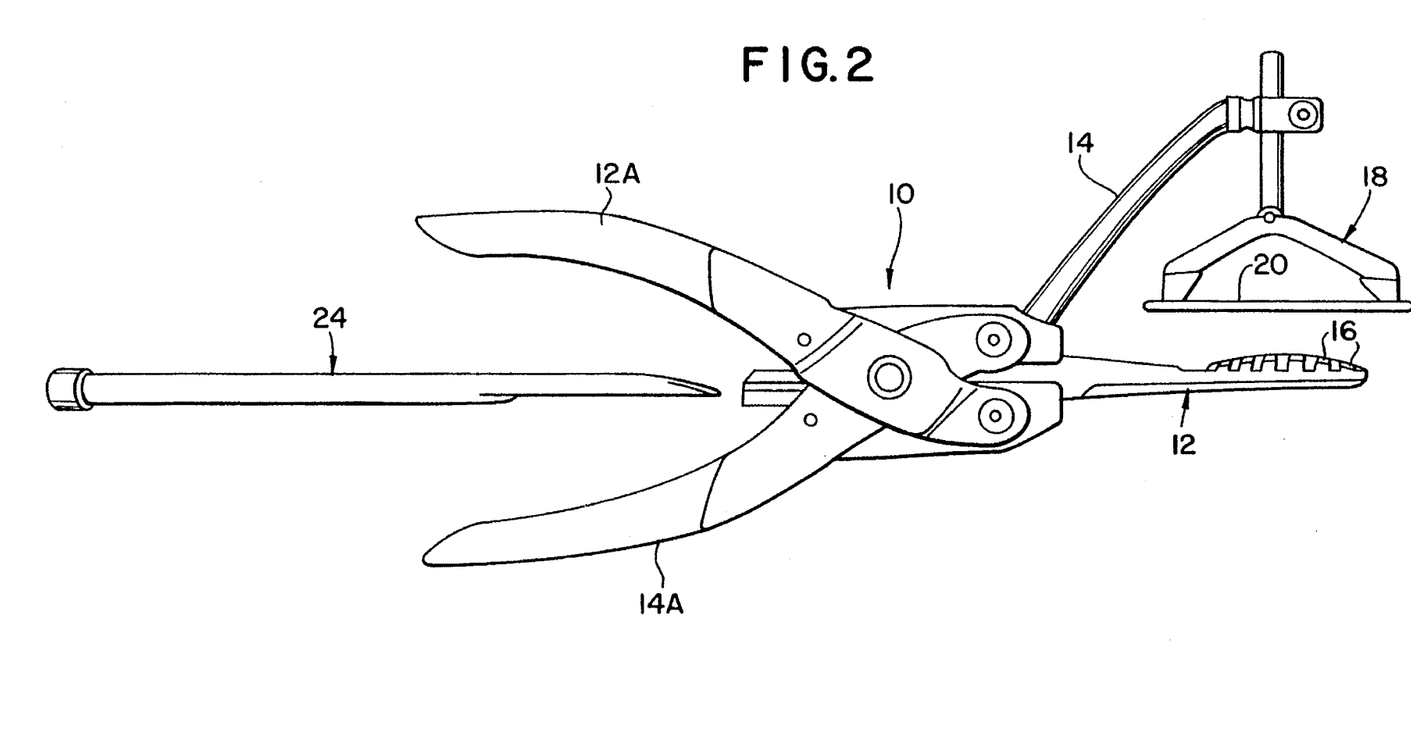
FIG. 2 is a side elevational view of the surgical instrument shown in FIG. 1, with a protector bar retracted.
Figure 3:
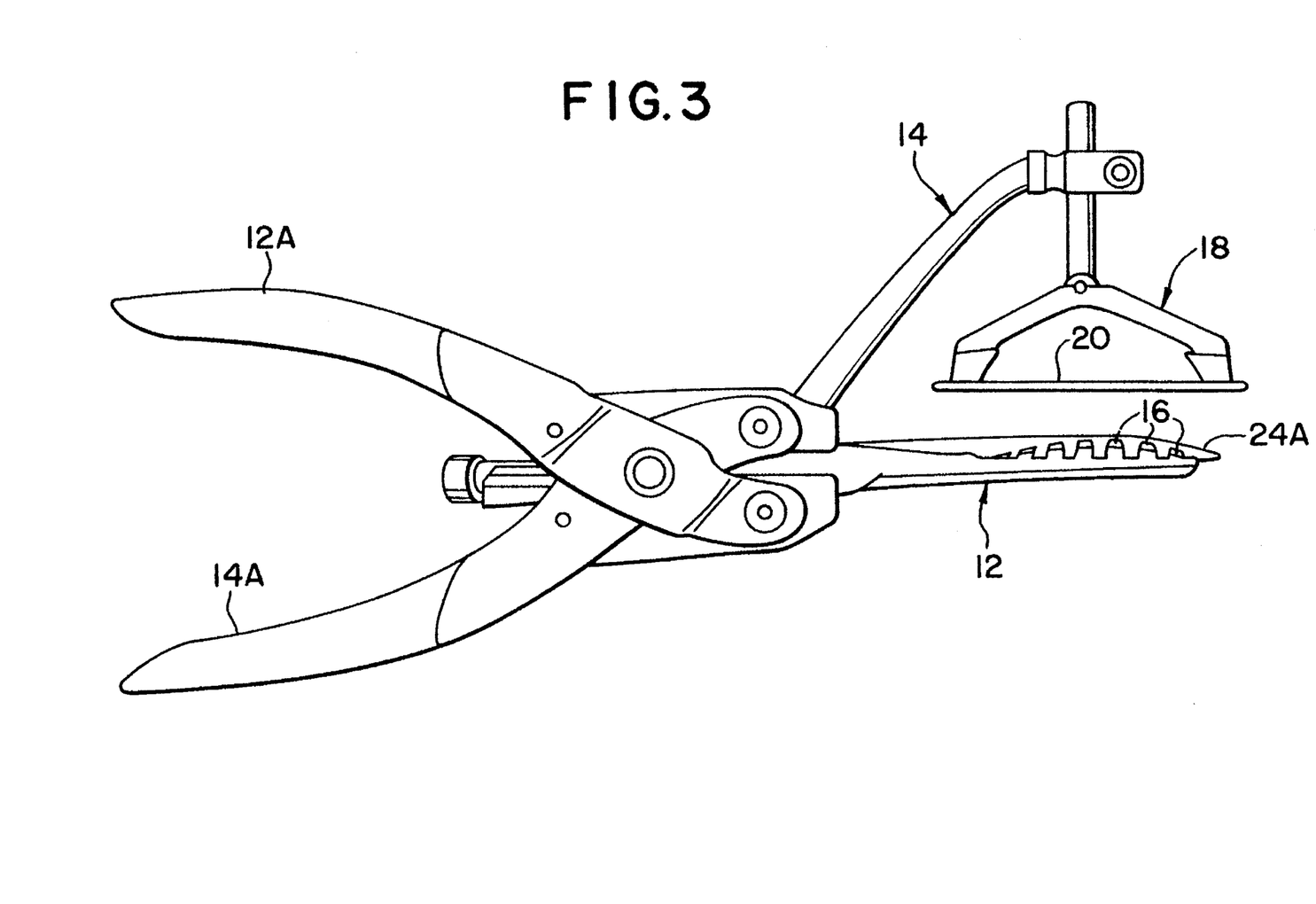
FIG. 3 is a side elevational view of the instrument shown in FIGS. 1 and 2, with the protector bar inserted between the spaced-apart rows of the teeth members.

FIGS. 1 and 2 also show an elongated protector bar 24 which can be slidably inserted into an aperture which extends through the length of arm 12. The forward end 24A of bar 24 is tapered. When the bar is fully inserted into the opening in arm 12, the forward end 24A of the bar is positioned between the rows of teeth 16 and provides a smooth tapered distal end for arm 12 to facilitate smooth insertion of arm 12 into the carpal tunnel of the patient through a small incision adjacent one end of the carpal tunnel. In FIG. 3 the bar 24 is fully inserted into arm 12.

The slider bar preferably includes a longitudinal bore which enables a conventional endoscopic system to be inserted therein, including means to illuminate and means to view. Aperture 24B serves as a viewing window. Thus, the proper position of the arm 12 in the carpal tunnel can be assured so that it cuts only the transverse carpal ligament and not other structures in the carpal tunnel.

Figure 8:
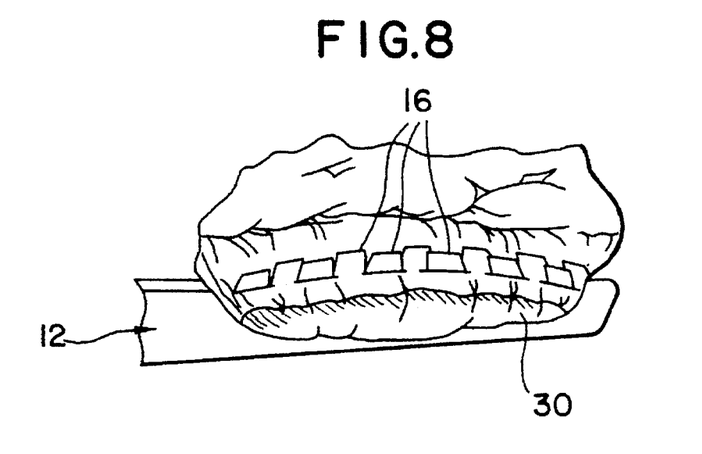
FIG. 8 is a perspective view showing the teeth members extending through the transverse carpal ligament.

As also illustrated in FIG. 3, the teeth 16 in each row provide a convex curved profile. In other words, the center teeth extend further palmarwardly than the teeth near the distal end and those nearer the proximal end. The reason for the curved profile is that the transverse carpal ligament has a similar curved profile (i.e., the transverse carpal ligament is thicker in the center and is thinner at its proximal and distal edges). This is illustrated in FIG. 8, for example.

As also observed in FIG. 3, when the slider bar 24 is inserted into the channel 12B between teeth members 16, the height of the bar 24 is at least equal to the height of the center (i.e., tallest) teeth. This protects the patient's carpal tunnel tissues from the teeth when arm 12 is inserted into the carpal tunnel, as illustrated in FIG. 6.

Figure 11:
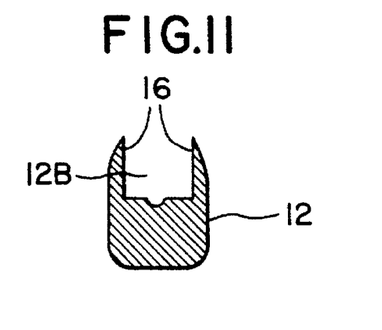
FIG. 11 is a cross-sectional view of the arm of the instrument showing the spaced-apart rows of teeth members.
Figure 12:
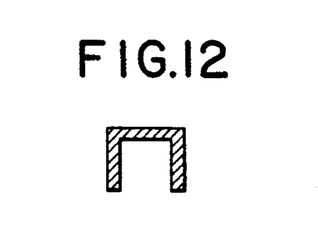
FIG. 12 is a cross-sectional view of another embodiment of protector means which is useful herein.

The teeth 16 are preferably tapered or bevelled at their upper ends and their distal and proximal ends, as shown in FIG. 11. As shown in the drawings, the proximal and distal teeth are shorter than the teeth in the central portion. The reason for this is because of the tapered or convex cross-sectional shape of the transverse carpal ligament (as shown in FIG. 8). Channel 12B between the two rows of teeth is only slightly wider than bar 24 so that bar 24 snugly fits into the channel. This arrangement assures that the teeth members are protected when the arm 12 is inserted into the carpal tunnel.

Figure 5:
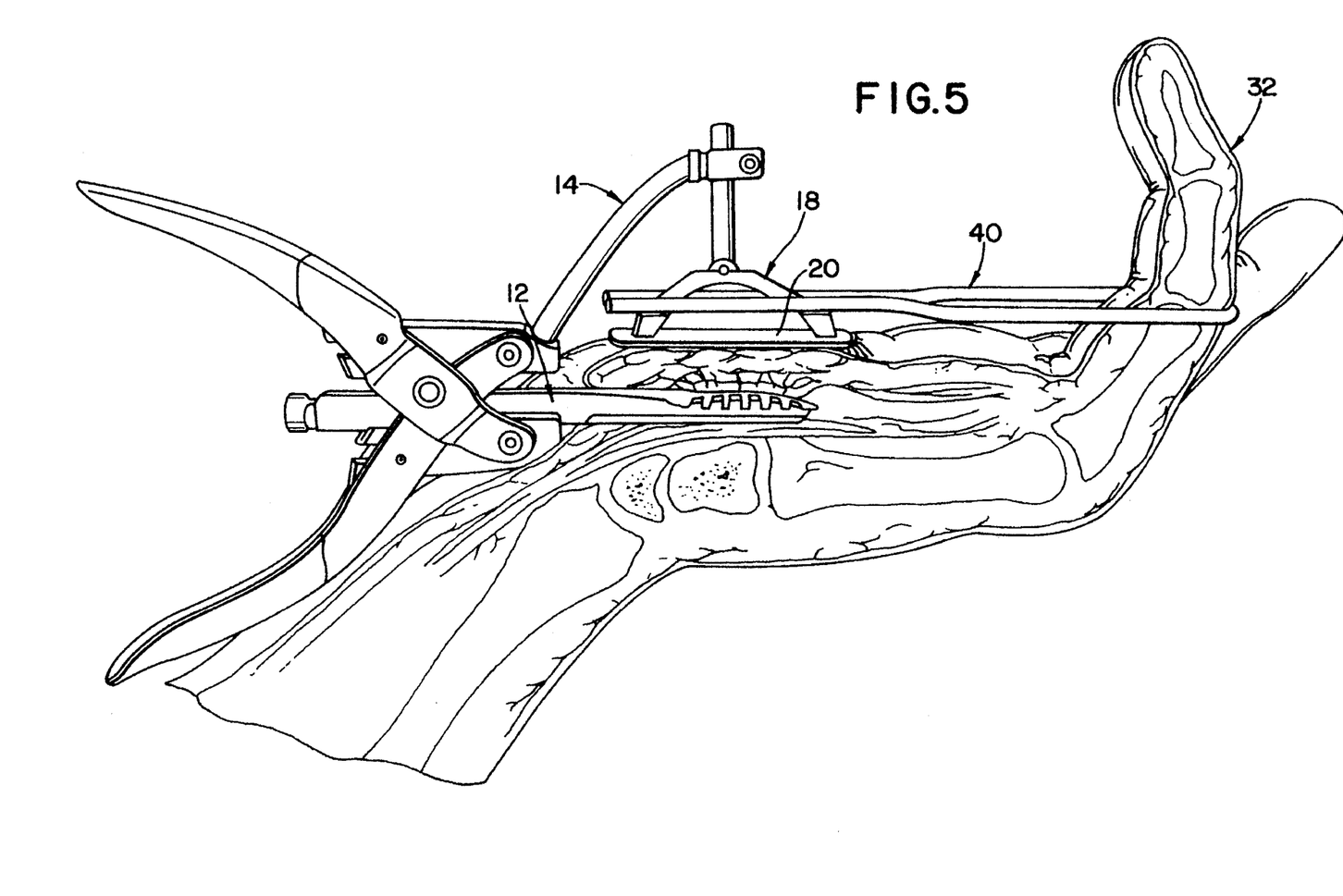
FIG. 5 is a cross-sectional view of the patient's hand with the instrument inserted into the carpal tunnel.
Figure 6:
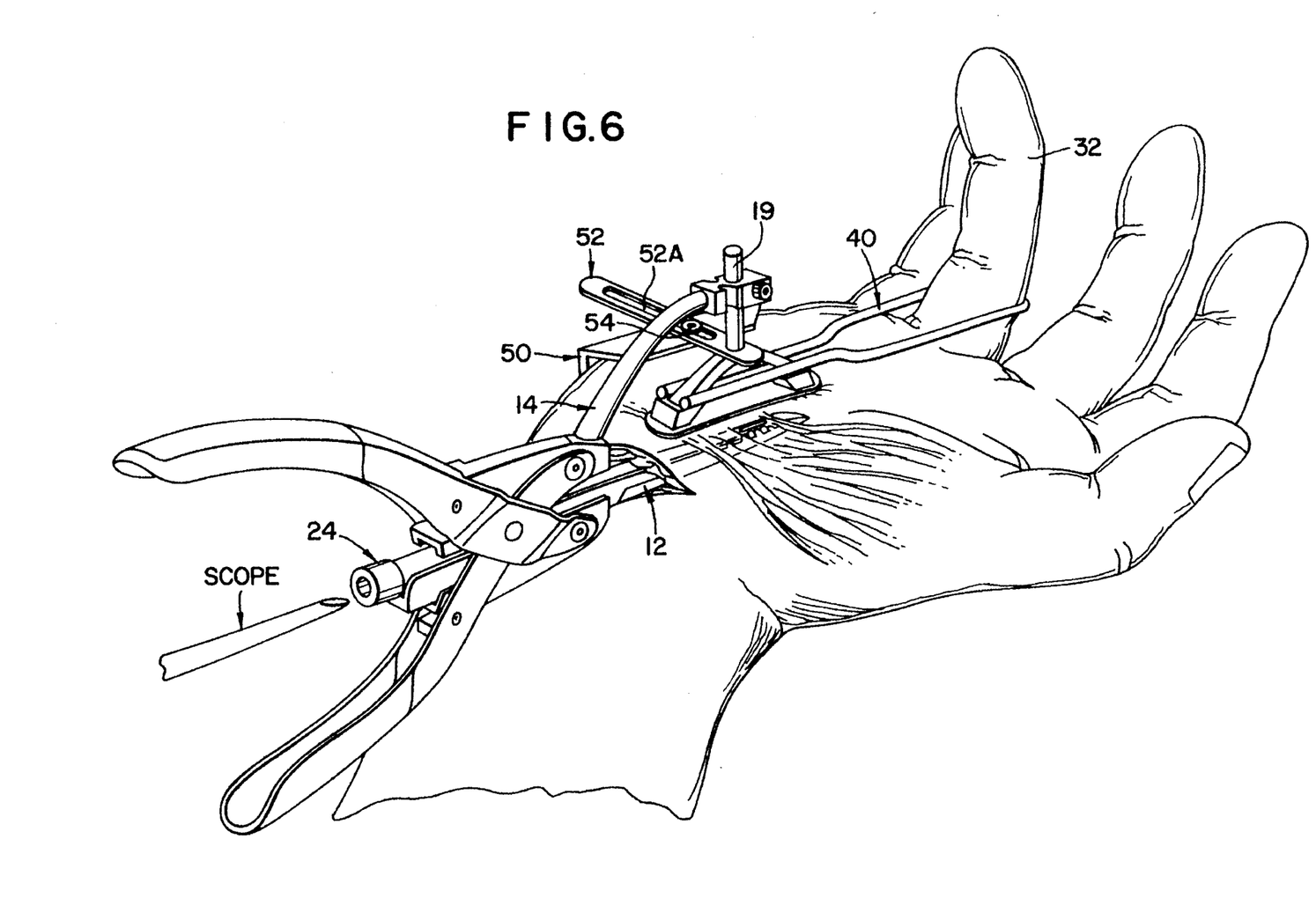
FIG. 6 is a perspective view illustrating the positioning of the teeth members of the instrument in the carpal tunnel of a patient.

After the arm 12 has been properly inserted into the carpal tunnel of the patient, as shown in FIG. 5, the protector bar is removed or retracted, as shown in FIG. 6. This exposes the teeth to the transverse carpal ligament.

Figure 7:
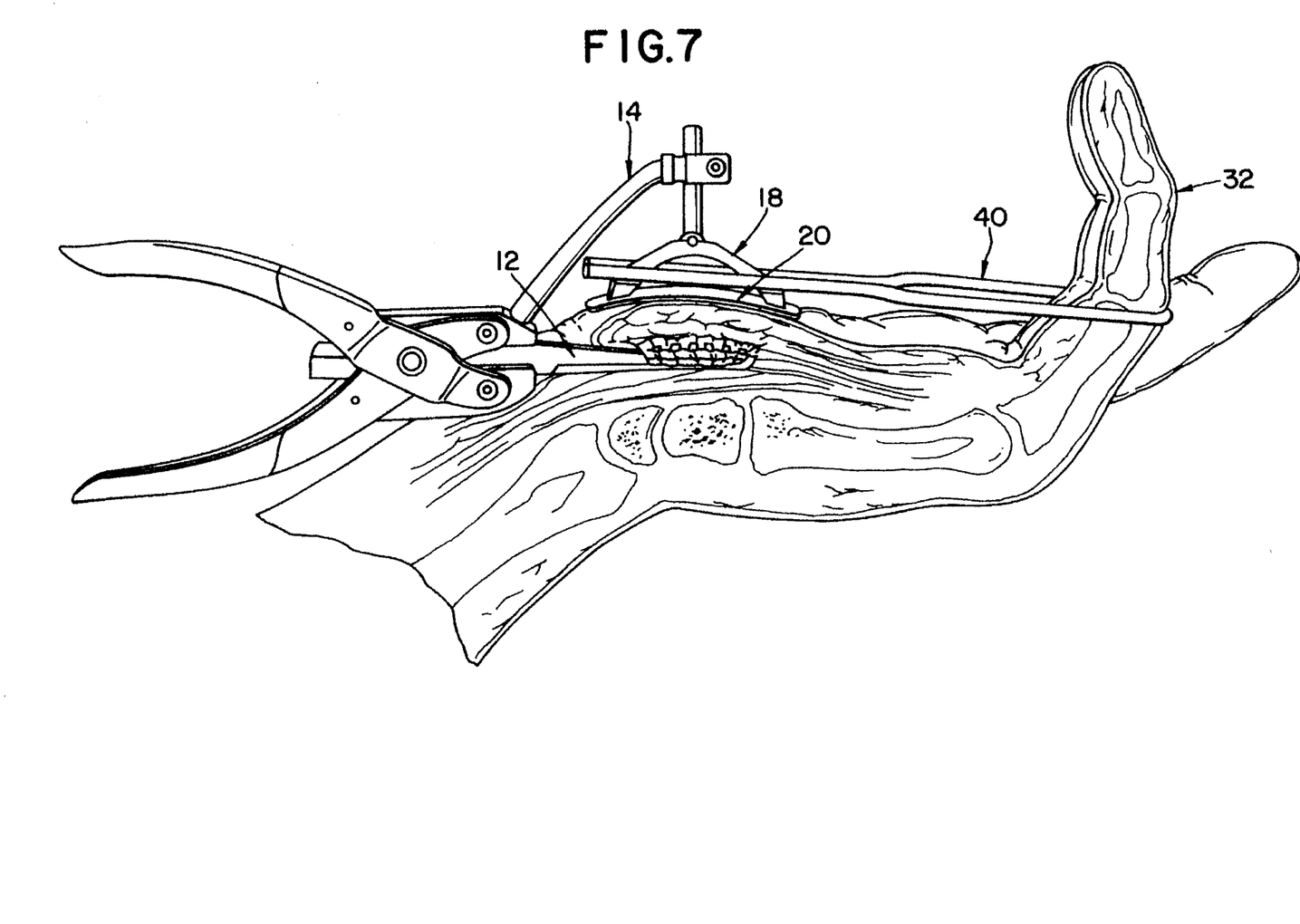
FIG. 7 is a cross-sectional view of the patient hand with the teeth members forced through the transverse carpal ligament.

Then the arms 12 and 14 can be moved towards each other in the manner shown in FIG. 7. This causes the teeth members 16 to be forced into and through the transverse carpal ligament to thereby perforate the ligament. This is also shown in FIG. 8.

FIG. 7 also illustrates that the press strip 20 deflects and conforms to the surface of the palm and heel of the patient when the arms 12 and 14 are urged towards each other. The force between arms 12 and 14 causes the teeth members to be forced through the transverse carpal ligament.

Figure 9:
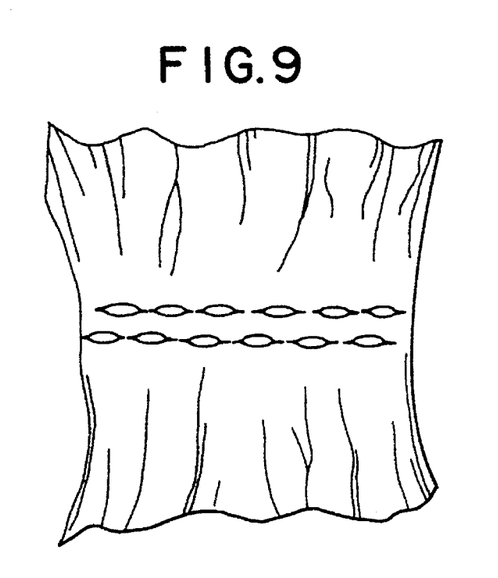
FIG. 9 is a dorsal view illustrating offset perforations made in the carpal ligament.

After the teeth have been forced through the transverse carpal ligament to perforate it, the transverse carpal ligament can stretch along its length to thereby decrease pressure in the carpal tunnel. In other words, these perforations increase the radial and ulnar length of the transverse carpal ligament thereby increasing the cross-sectional area of the carpal tunnel and decreasing the pressure therein. This is illustrated in FIG. 9 which shows the transverse carpal ligament 30 and the staggered apertures or openings 30A formed by the teeth 16.

After the teeth 16 have cut through the transverse carpal ligament, the protector bar 24 is again inserted into the channel 12B in arm 12 between the rows of teeth 16. This causes the ligament to be lifted off the teeth 16 and also enables arm 12 to be safely removed from the carpal tunnel.

Figure 4:
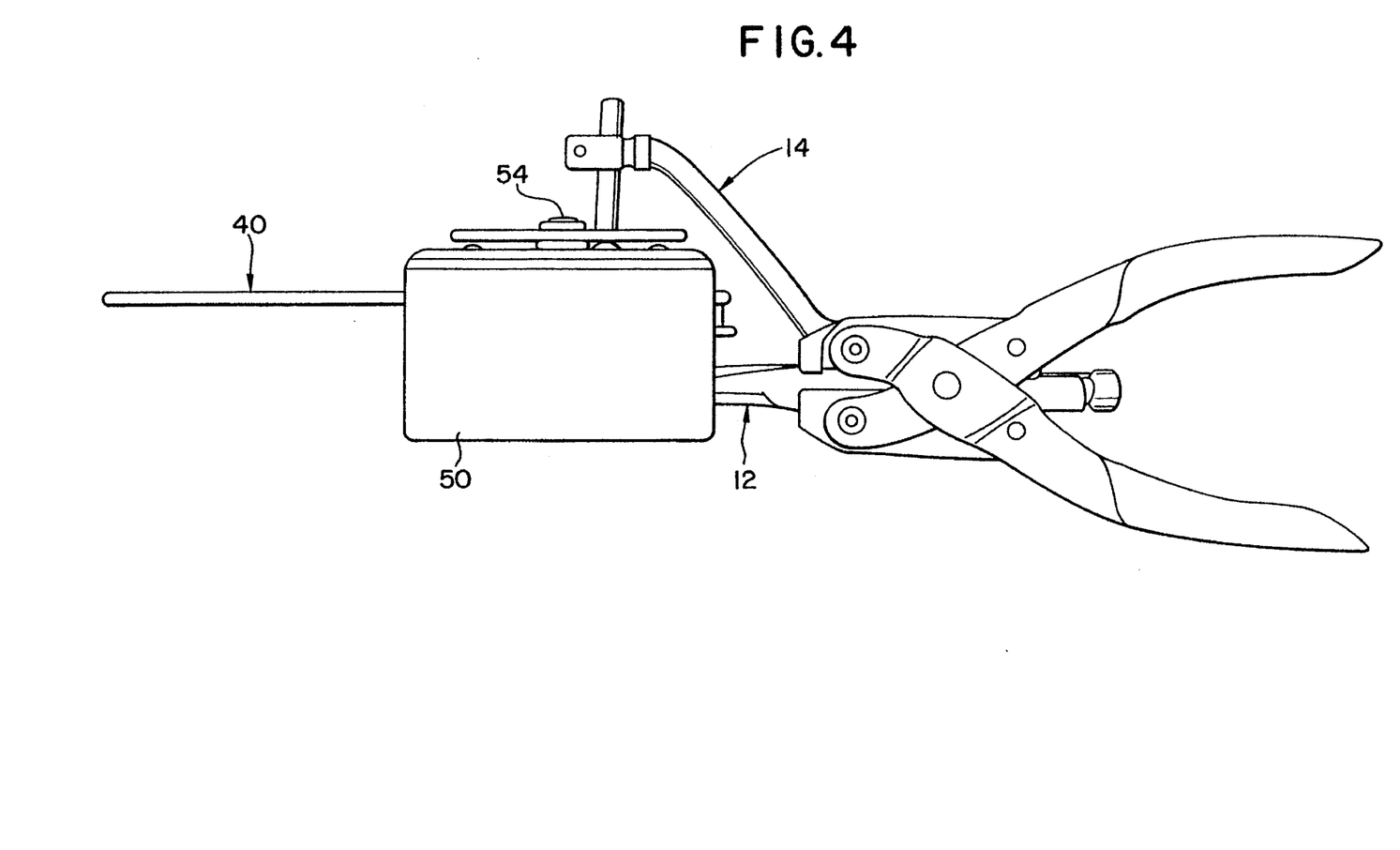
FIG. 4 is a side elevational view of the instrument of FIG. 1 which further includes a guide system as an aid in inserting the instrument into the carpal tunnel.

Also illustrated in the drawings is a guide system which greatly facilitates safe and effective use of the surgical instrument. The guide system includes an elongated arm 40 which is carried by press member 18. The distal end of arm 40 encircles or otherwise engages the ring finger 32 of the patient.

The guide system also includes vertical plate member 50 which is carried on transverse arm 52 secured to shank 19. The lateral position of plate 50 may be adjusted by means of screw 54 in slotted aperture 52A.

By engaging arm 40 on the ring finger, and by orienting the surgical instrument such that the vertical plate 50 is in contact with the ulnar border of the hand, the arm 12 is thereby properly oriented with respect to the hand for safe insertion into the carpal tunnel.

Figure 13:
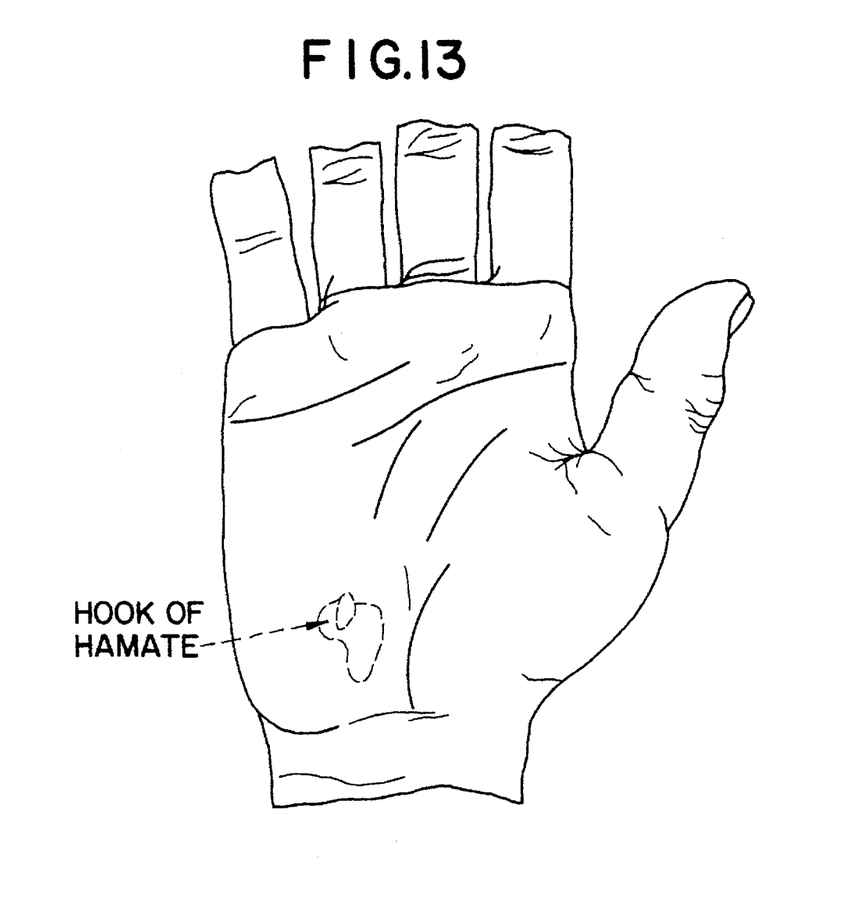
FIG. 13 is a plan view of the palmar side of a hand showing the location of the hook of the hamate.

This system of an ulnar border guide 50 and a mechanism for aiming the device down the ulnar side of the carpal tunnel toward the ring finger facilitates the safe insertion of the instrumentation for cutting the transverse carpal ligament, i.e., probe 12. Anatomically, insertion of instrumentation down the ulnar side of the carpal tunnel along a path adjacent to the hook of the hamate and aiming at the ring finger assures the exposure of the instrumentation to a portion of the transverse carpal ligament that is free of precious structures. Adjustment of vertical plate member 50 by screw 54 in slotted aperture 52A allows proper spacing of the cutting probe 12 so that it can, with assurance, remain snugly against the ulnar side of the carpal tunnel adjacent to the hook of the hamate bone while arm 40 encircling the proximal segment of the ring finger assures aiming of the device in the direction of the ring finger. FIG. 13 shows the location of the hook of the hamate in the hand.

Therefore, this guide system assures the three major elements of the safe insertion of an instrument for cutting the transverse carpal ligament that is inserted from a single proximal portal at or just proximal to the wrist flexion crease. The probe is inserted just deep to the transverse carpal ligament adjacent to the hook of the hamate and aimed at the ring finger. In addition, the tip of the probe should not extend much beyond the distal end of the carpal tunnel.

Other variations in the guide system are also possible so long as it references the distance between the ulnar border of the hand and the ulnar side of the carpal tunnel (as defined by the radial surface of the hook of the hamate) and therefore is able to maintain a probe snug against the hook of the hamate. The guide system disclosed herein, and variations of it, is useful in connection with any type of probe to be inserted in the carpal tunnel. The ring finger serves as an accurate aim point only when its base or metacarpophalangal joint is flexed, as illustrated. When the M.P. joint is flexed to 90°, the proximal segment cannot be displaced in a radial or ulnar direction and therefore it is a stable post for aiming a probe into the carpal tunnel.

Arm 40 is not only useful for aiming a probe at the ring finger but it also is useful for maintaining the M.P. joint of the ring finger in a flexed position so that it is an effective anatomical landmark for aiming the probe down the ulnar side of the carpal tunnel.

Variations of plate 50 and arm 52 are also possible. Anatomically, there is a fixed distance between the ulnar side of the hand and the surface of the hook of the hamate that is exposed to the ulnar side of the carpal tunnel. Other means for referencing this distance may be used to ensure proper positioning of the probe in the carpal tunnel.

Although the probe system described and illustrated herein is the preferred apparatus for practicing the present invention, other apparatus may also be used for selective cutting or perforating the transverse carpal ligament. For example, the teeth on the probe may be covered with a removable shield until the probe is properly positioned in the carpal tunnel. Preferably, the teeth are positioned in a plurality of spaced-apart rows (as illustrated in the drawings), although that is not required.

Other variants are possible without departing from the scope of this invention. For example, the apparatus describe herein for perforating the transverse carpal ligament may include any desired number of teeth members which may be present in any desired number of rows (e.g., 2, 3, 4, etc.) or they may be randomly disposed. The teeth may be covered or otherwise prevented from cutting tissue in any desired manner when the probe is inserted into the carpal tunnel, after which the teeth may be exposed for perforating the transverse carpal tunnel. Although it is preferred to use the apparatus of this invention in conjunction with an endoscope, this is not absolutely required.

What is claimed is:

1. A guide system for guiding a probe into the carpal tunnel of a patient, wherein said probe is carried by handle means, said guide system comprising:

(a) an elongated leg member supported by said handle means for engaging a finger of the patient's hand, and (b) a vertical edge guide member supported by said handle means for engaging the edge of the patient's hand;

wherein said guide member is adapted to maintain lateral alignment of said probe with respect to the carpal tunnel of said patient; and (c) means for holding said probe in alignment with the carpal tunnel of a patient's hand.

2. A guide system in accordance with claim 1, wherein said leg member comprises a U-shaped bar for engaging a flexed finger of the patient's hand.

3. A guide system in accordance with claim 1, wherein said edge guide member comprises a planar plate member.

4. A guide system in accordance with claim 1, further comprising a transverse arm member having a first end attached to said handle means; wherein said edge guide member is carried on said arm member.

5. A guide system in accordance with claim 4, wherein said edge guide member is laterally adjustable on said transverse arm member.

\* \* \* \* \*